(12) United States Patent
Crowley et al.

(10) Patent No.: US 6,238,348 B1
(45) Date of Patent: May 29, 2001

(54) MINIATURE SPECTROMETER SYSTEM AND METHOD

(75) Inventors: Robert J. Crowley, Sudbury; Mark Hamm, Lynnfield, both of MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 09/167,824

(22) Filed: Oct. 7, 1998

Related U.S. Application Data

(63) Continuation-in-part of application No. 08/903,218, filed on Jul. 22, 1997, and a continuation-in-part of application No. 08/898,604, filed on Jul. 22, 1997, and a continuation-in-part of application No. 08/922,263, filed on Sep. 2, 1997, and a continuation-in-part of application No. 08/939,612, filed on Sep. 29, 1997, and a continuation-in-part of application No. 08/940,464, filed on Sep. 29, 1997, and a continuation-in-part of application No. 08/939,707, filed on Sep. 29, 1997, and a continuation-in-part of application No. 08/939,706, filed on Sep. 29, 1997

(60) Provisional application No. 60/061,690, filed on Oct. 10, 1997.

(51) Int. Cl.⁷ .................................................. A61B 6/00
(52) U.S. Cl. ................................................... 600/476
(58) Field of Search .................................. 600/476, 477, 600/478, 310

(56) References Cited

U.S. PATENT DOCUMENTS

| 5,131,398 | 7/1992 | Alfano et al. ................... 128/665 |
| 5,172,693 | 12/1992 | Doody ............................ 128/633 |
| 5,193,542 | 3/1993 | Missanelli et al. ............. 128/633 |
| 5,785,658 | * 7/1998 | Benaron et al. ................ 600/473 |
| 5,984,861 | * 11/1999 | Crowley ......................... 600/175 |

FOREIGN PATENT DOCUMENTS

| 0 650 694 A1 | 5/1995 | (EP) . |
| WO 92/12536 | 11/1990 | (WO) . |
| WO 95/12349 | 5/1995 | (WO) . |
| WO 99/22805 | 5/1998 | (WO) . |

* cited by examiner

*Primary Examiner*—Marvin M. Lateef
*Assistant Examiner*—Eleni Mantis Mercader
(74) *Attorney, Agent, or Firm*—Testa, Hurwitz & Thibeault, LLP

(57) ABSTRACT

A miniature spectrometer can be used in situ to diagnose tissue and organs by detecting tissue autofluorescence. The miniature spectrometer is disposed at the distal end of an interventional device.

18 Claims, 11 Drawing Sheets

(0.105" x 0.043")

9.3f (0.128" Dia.)

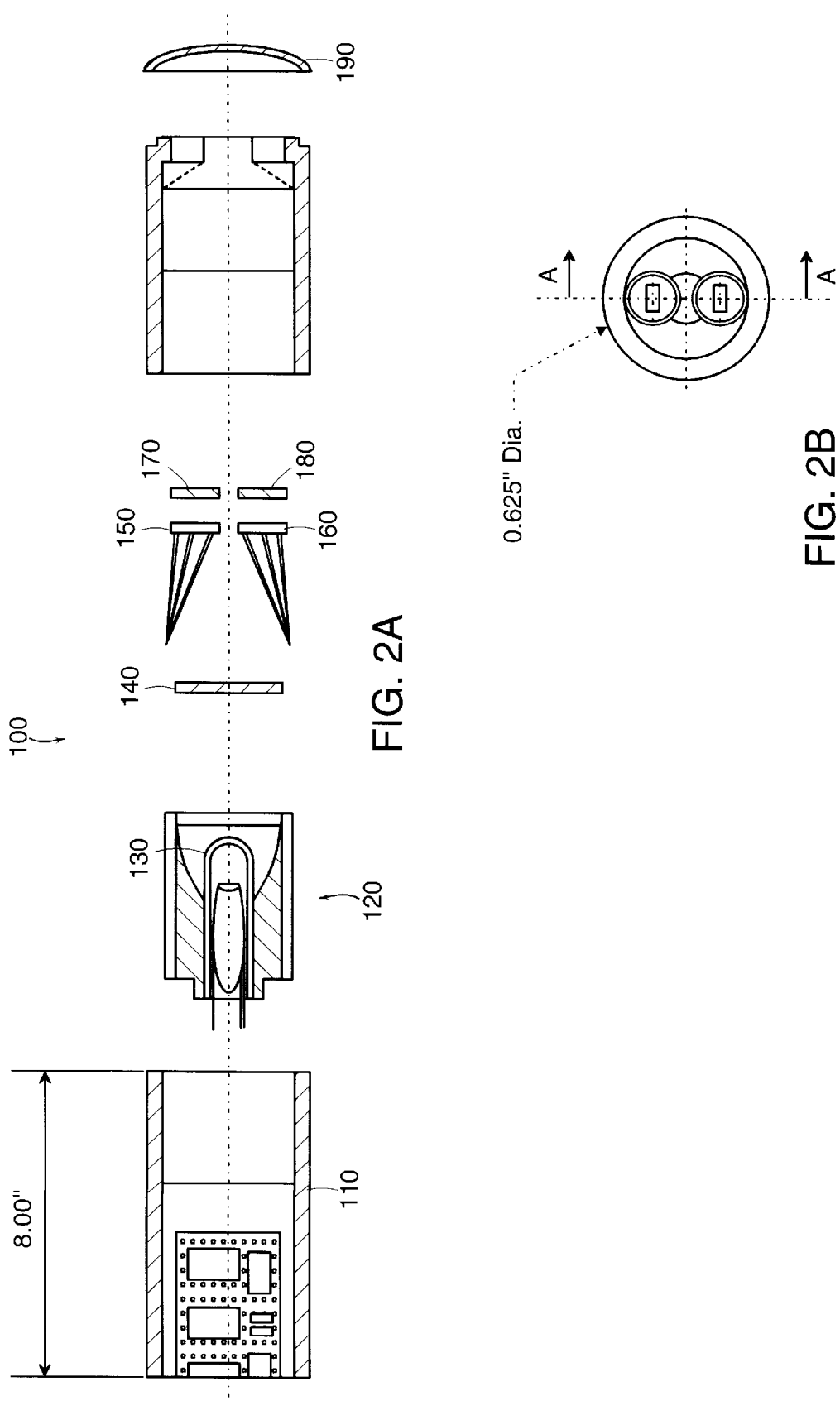

MINIATURE SPECTROMETER SYSTEM AND METHOD

RELATED APPLICATIONS

This application is based on, and claims priority to, U.S. Provisional Patent Application Serial No. 60/061,690, filed on Oct. 10, 1997, and is a continuation-in-part of U.S. patent application Ser. No. 08/903,218, filed on Jul. 22, 1997, U.S. patent application Ser. No. 08/898,604, filed on Jul. 22, 1997, U.S. patent application Ser. No. 08/922,263, filed on Sep. 2, 1997, U.S. patent application Ser. No. 08/939,612, filed on Sep. 29, 1997, U.S. patent application Ser. No. 08/940,464, filed on Sep. 29, 1997, U.S. patent application Ser. No. 08/939,707, filed on Sep. 29, 1997, and U.S. patent application Ser. No. 08/939,706, filed on Sep. 29, 1997.

TECHNICAL FIELD

This invention relates to the in situ diagnosis of tissue and organs through the use of interventional spectrometry.

BACKGROUND INFORMATION

Illumination of tissue can induce endogenous tissue fluorescence, also known as autofluorescence. The spectrum emitted by tissue autofluorescence can be characteristic of a tissue's underlying condition. For example, when illuminated with 370 nm light, the spectrum emitted from normal mucosa differs from that of an adenoma. Tissue autofluorescence spectrometry can thus be employed to diagnose cancerous conditions such as adenoma. Other conditions that can be identified by tissue autofluorescence include arteriosclerosis.

Tissue fluorescence may be based on intrinsic properties of the tissue, or on the differential uptake of a fluorophore administered before the spectrometry is performed.

Interventional tissue autofluorescence spectrometry is known in the art. Currently known devices locate the spectrometer at the proximal end of the interventional device, i.e. outside the patient. These devices rely on fiber optic bundles to transmit light between the analysis site and the externally-located spectrometer. The limitations inherent in employing fiber optic bundles are threefold. First, they are expensive. Second, they are stiff, lacking flexibility and maneuverability. Third, they are large, requiring a relatively large diameter to transmit the necessary amount of light to and from the analysis site. Currently known interventional spectrometry devices are thus limited to use in relatively large and straight passages, such as the gastrointestinal tract.

SUMMARY OF THE INVENTION

This invention relates to an interventional device with a spectrometer at its distal end. The spectrometer can be used to perform an in vivo analysis of a tissue's fluorescence characteristics, which can be used in diagnosing conditions such as cancer.

It is an object of this invention to place a spectrometer at the distal end of an interventional device with a small enough form factor to be useful in diagnosing a large variety of tissues and organs in situ.

It is a further object of this invention to provide a means of communication between the distal and proximal ends of the interventional device that is flexible and narrow, thus allowing the device to be used in a variety of passageways throughout the body. It is a further object of the invention that the means of communication be inexpensive, such as a copper wire.

The spectrometer comprises a source unit for emitting light at a certain frequency or a plurality of frequencies. The spectrometer further comprises a plurality of sensors for measuring light at a plurality of frequencies.

The source unit comprises a light source. The light source can be monochromatic or polychromatic. In one embodiment, a tungsten-halogen light is employed as a polychromatic light source. If a polychromatic light source is used, a bandpass filter may be attached. The bandpass filter may allow one or more frequencies to pass through. The frequencies emitted by the source unit are selected to provide data diagnostic of a tissue's condition. In one embodiment, the source unit emits light at a frequency of 435 nm. In other embodiments, the source unit may emit light at a frequency of 420 nm, 490 nm, or any combination thereof.

Similarly, the frequencies measured by the sensors are selected to provide data diagnostic of a tissue's condition. In one embodiment, the spectrometer comprises two sensors, which measure light at wavelengths of 370 nm and 440 nm, respectively.

Another object of this invention is to minimize the waste heat generated by the spectrometer. In one embodiment, the source unit emits 200 μw or less. In another embodiment, the surface of the distal end of the interventional device does not exceed a temperature of 40 degrees Celsius after 30 seconds of continuous operation. In one embodiment of the invention, the source unit is activated in brief pulses in order to keep heat down to a minimum.

BRIEF DESCRIPTION OF THE DRAWINGS

FIG. 2A is an exploded cross-sectional side view of a clinically-sized end-looking device, with the cross section being taken along line A–A in FIG. 2B.

FIG. 2B is an end of view of the device of FIG. 2A.

DESCRIPTION

Figure 1A:
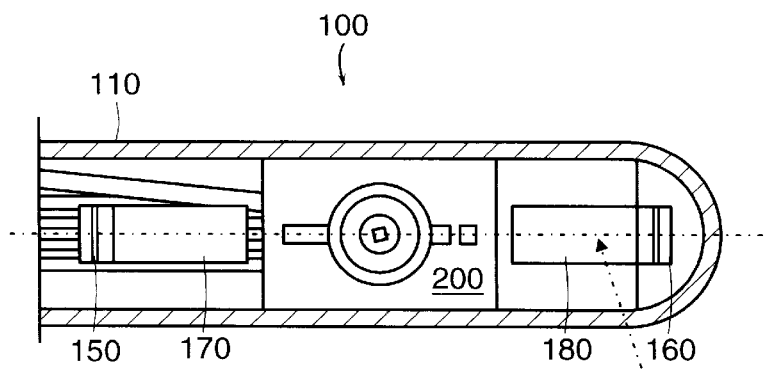
FIG. 1 depicts a side-looking embodiment of a spectrometer comprising a 435 nm LED and two sensors.
Figure 1B:
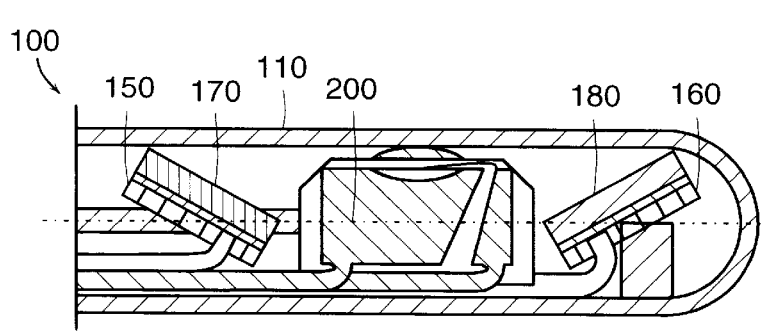
Figure 1C:
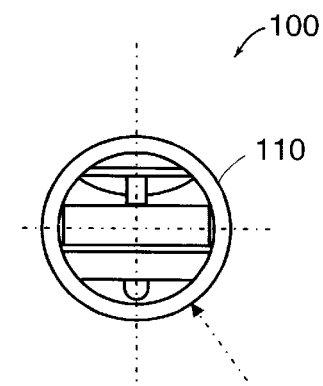

In one embodiment, depicted in FIG. 1, the spectrometer 100 is contained in a housing 110 with a diameter of 9.3 F (0.128 inches) and a wall thickness of 0.015 inches. This embodiment employs as its light source a LED 200 which emits light at a frequency of 435 nm. This embodiment further employs two PIN photodiodes as sensors 150 and 160, disposed on either side of the LED 200. Attached to each sensor 150 and 160 is a bandpass filter 170 and 180 that lets through 370 nm and 440 nm, respectively. The LED and sensors are disposed along the longitudinal axis of the housing 110, and face in a direction perpendicular to the longitudinal axis. In a preferred embodiment, the sensors are angled inward towards the LED 200. The housing 110 is transparent, and is designed to minimize attenuation of both excitation and emitted energy. In a further preferred embodiment, the LED 200 and the PIN photodiodes 150 and 160 are made with single layer construction. In yet another embodiment, the LED 200 is a LEDtronics model 435.

In another embodiment, depicted in FIGS. 2A and 2B, the spectrometer 100 is contained in a housing 110 with a diameter of 0.625 inches, and an overall length of 8 inches. In this embodiment, the light source 120 is a tungsten-halogen bulb 130 with a bichromatic filter 140 attached. The bichromatic filter 140 only lets through light with wavelengths of 420 nm and 490 nm. This embodiment employs two PIN photodiodes 150 and 160 as sensors. Attached to each sensor is a bandpass filter 170 and 180 that lets through 370 nm and 440 nm, respectively. The light source 120 is disposed along the longitudinal axis of the housing 110 and faces the distal end of the housing 110. Similarly, the sensors 150 and 160 face the distal end of the housing, and are disposed on either side of the longitudinal axis. An end cap 190 covers the distal end of the housing. The end cap is designed to minimize attenuation of both excitation and emitted energy. In a preferred embodiment, the sensors are angled inward about 30 degrees towards the longitudinal axis.

Figure 3:
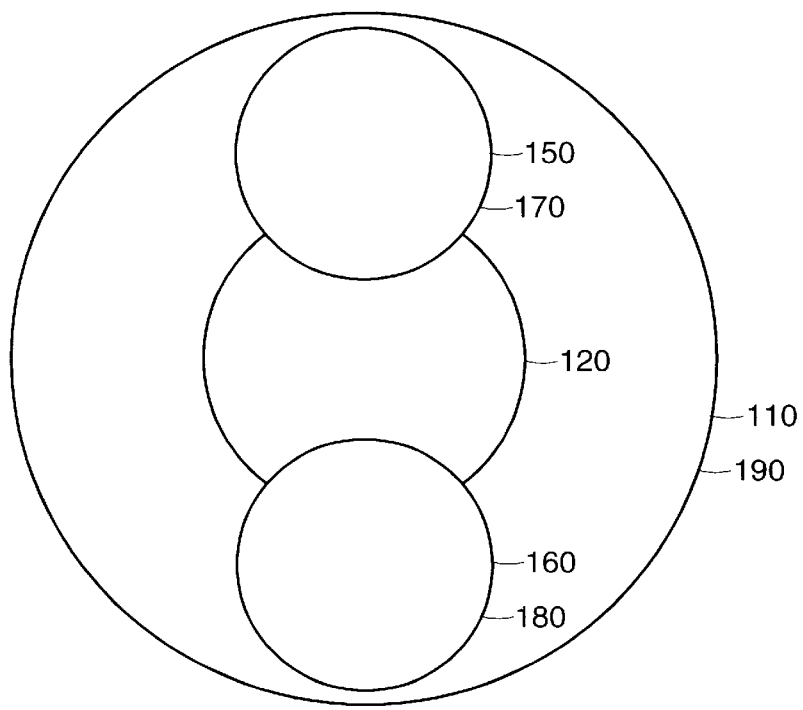
FIG. 3 shows the distal end of the clinically-sized device of FIGS. 2A and 2B.

In FIG. 3, the sensors 150 and 160, their filters 170 and 180, as well as the light source 120 are visible through the end cap 190.

Figure 4:
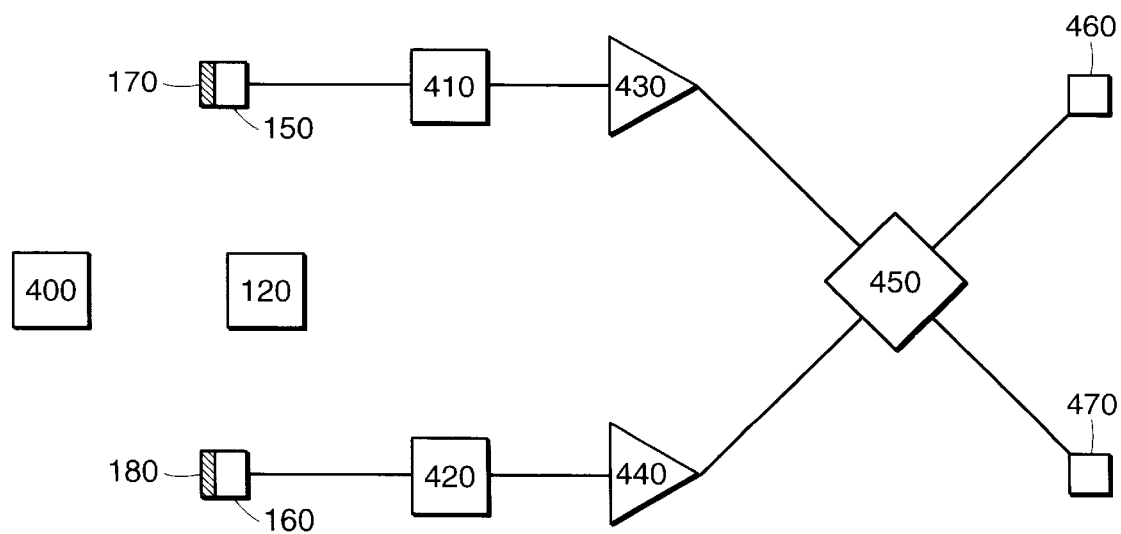
FIG. 4 depicts an electronics block diagram for the clinically-sized device of FIGS. 2A and 2B.

FIG. 4 depicts an electronics block diagram for the embodiment depicted in FIG. 2 and FIG. 3. In this embodiment, the test sample 400 fluoresces at wavelengths of 440 nm and 370 nm when illuminated by 300 nm light from light source 120. Filters 170 and 180 are attached to PIN photodiodes 150 and 160, respectively. Bandpass filters 170 and 180 let through light of 440 nm and 370 mn, respectively. PIN photodiodes 150 and 160 emit an electrical signal in response to light. The strength of their signals is proportional to the intensity of the light shining on them. These electrical signals are sent through low pass filters 410 and 420. These filters remove 60 Hz electrical signals, and serve to increase the signal-to-noise ratio of the output of the PIN photodiodes 150 and 160. The signals are next sent to amplifiers 430 and 440, and combined into a comparator decision process 450. Depending on the signals' relative intensities, the comparator decision process 450 indicates either result A 460 or result B 470.

In an embodiment of the comparator decision process 450, colonic tissue is diagnosed for adenoma. The colon is illuminated with 325 nm light, and tissue autofluorescence readings are taken at 460 nm and 680 nm. A numeric result, C, is calculated according to the following formula, C=A * (tissue autofluorescence at 460 nm)+B * (tissue autofluorescence at 680 nm), where A and B are constants set according to the relative autofluorescent characteristics of normal and adenomous tissue. If C is above some threshold value, T, then the tissue is diagnosed as an adenoma.

In a preferred embodiment of this invention, the light source operates in the "blue" region of the visible spectrum, emitting light at a wavelength or wavelengths selected from a region between 400 nm and 490 nm.

Figure 5:
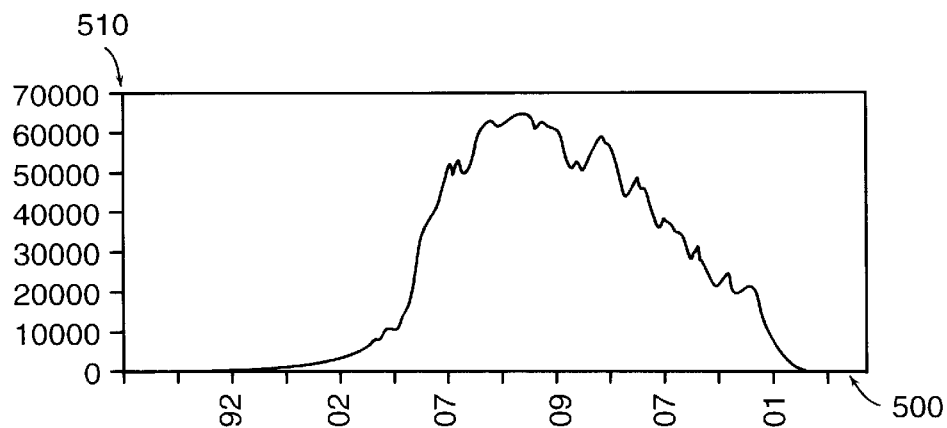
FIG. 5 depicts the emission spectrum of a tungsten-halogen lamp.

For the purposes of tissue autofluorescence spectrometry, a light source emitting light at a wavelength of 300 nm is desirable. FIG. 5 depicts the output spectrum of a tungsten-halogen lamp. The units along x-axis 500 represent the wavelength of the light emitted by the light source in nanometers. The units along the y-axis 510 represent the intensity of the light in a.u. The spectrum indicates that the lamp emits a useful amount of light in the 300 nm range.

Figure 6:
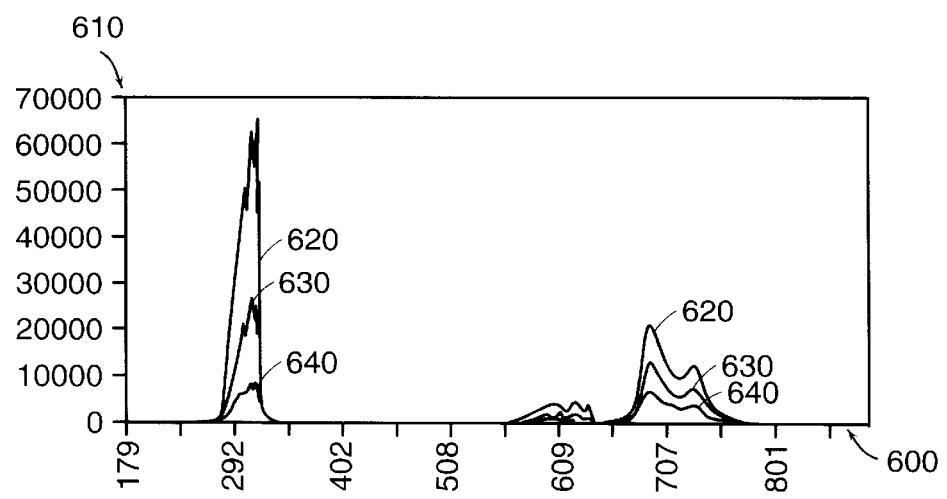
FIG. 6 depicts the excitation intensity of a filtered tungsten-halogen lamp.

FIG. 6 depicts output spectra of a tungsten-halogen lamp with a bichromatic filter attached. The units along the x-axis 600 represent the wavelength of the light emitted by the light source in nanometers. The units along the y-axis 610 represent the intensity of the light in a.u. Emission curve 620 depicts the output spectrum when 7V is applied. Emission curve 630 depicts the output spectrum when 6V is applied. Emission curve 640 depicts the output spectrum when 5V is applied. The intensity of the spectrum varies as a result of the voltage used. A large increase in light output at 300 nm is observed when the voltage is increased from 5V to 7V.

Figure 7:
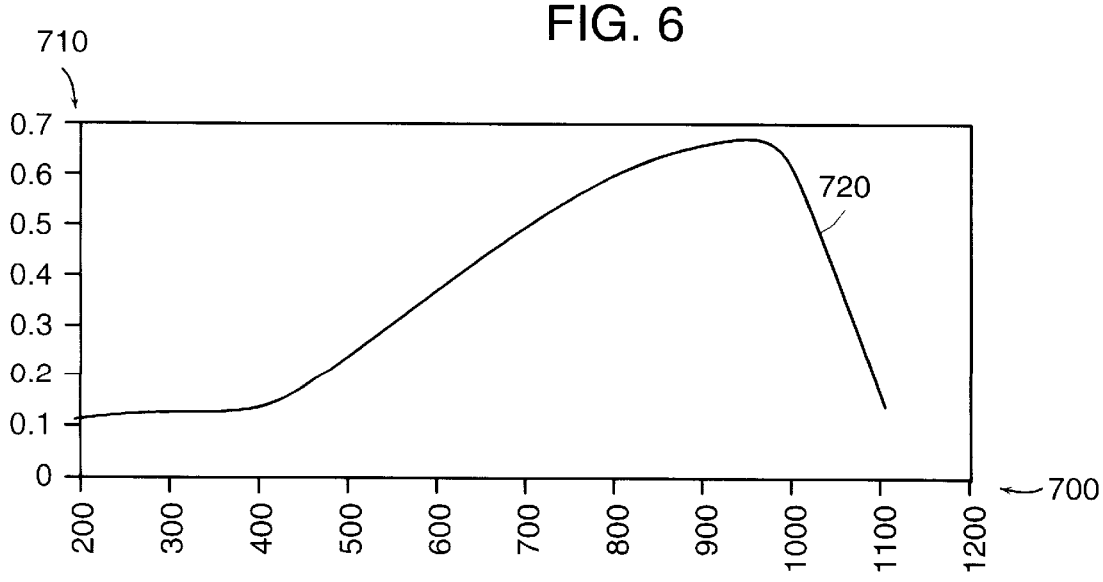
FIG. 7 depicts a PIN photodiode response as a function of wavelength.

For the purposes of this invention, it is necessary that the sensors are able to respond to the light at wavelengths at which the tissues to be examined autofluoresce. FIG. 7 depicts the spectrum response of a PIN photodiode. The units along x-axis 700 represent the wavelength of light input into the sensor in nanometers. The units along the y-axis 710 represent the response of the photodiode in A/W. As evidenced from the response curve 720, the PIN photodiode reacts to a broad spectrum of light.

Figure 8A:
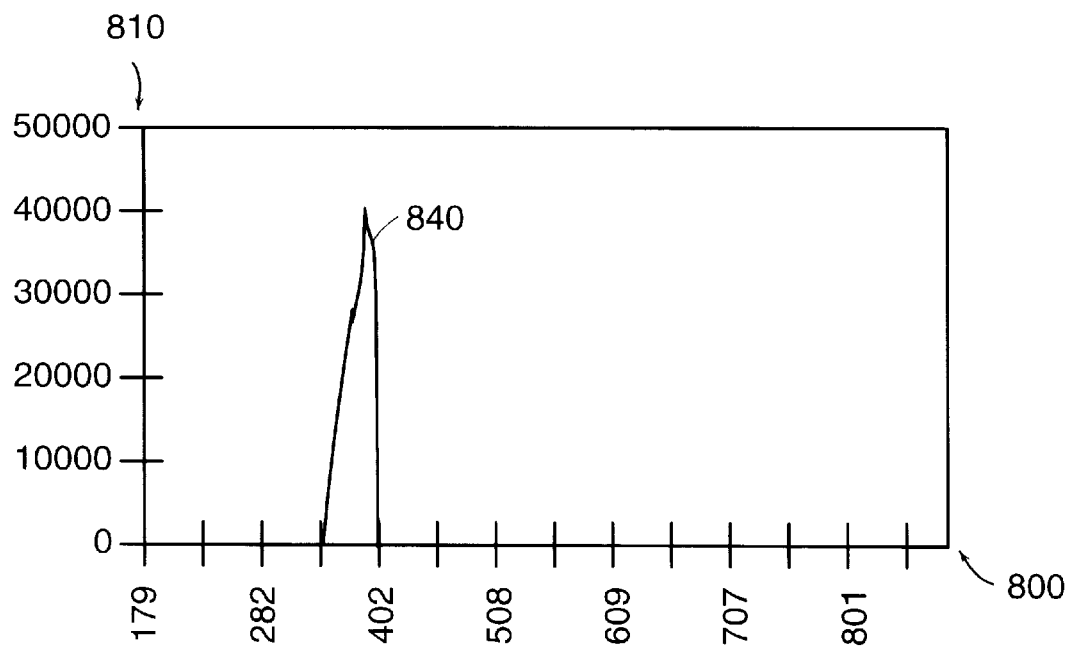
FIG. 8A depicts the wavelengths of light let through a 370 nm bandpass filter.
Figure 8B:
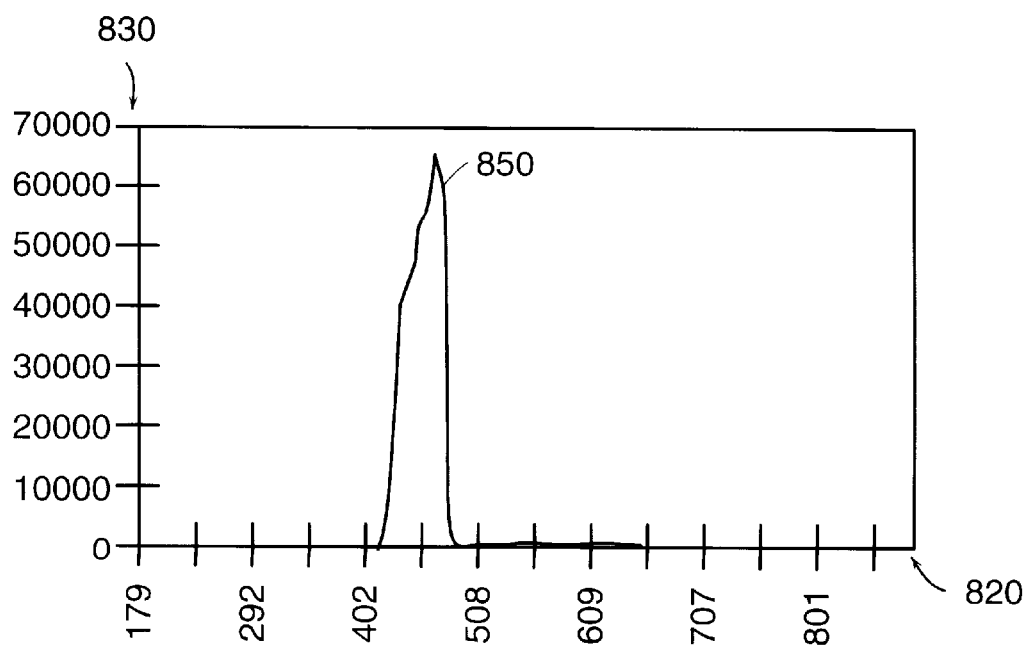
FIG. 8B depicts the wavelengths of light let through a 400 nm bandpass filter.

For the purposes of this invention it is further necessary that a sensor responds only to specific wavelengths of light, and not respond to light outside its designated wavelength. FIG. 8A and FIG. 8B depict two photoresponse curves of a PIN photodiode. The units along the x-axes 800 and 820 represent the wavelength of the light input into the sensor in nanometers. The y-axes 810 and 830 represent the transmission in a.u. FIG. 8A depicts the photoresponse curve of a PIN photodiode with a 370 nm bandpass filter attached. Similarly, FIG. 8B depicts the photoresponse curve of a PIN photodiode with a 400 nm bandpass filter attached. As evidenced by photoresponse curve 840, the PIN photodiode with a 370 nm bandpass filter attached responds only to a narrow range of wavelengths centered around 370 nm. Response to wavelengths outside of this range is essentially zero. Response curve 850 depicts analogous results for the 400 nm bandpass filter.

Figure 9:
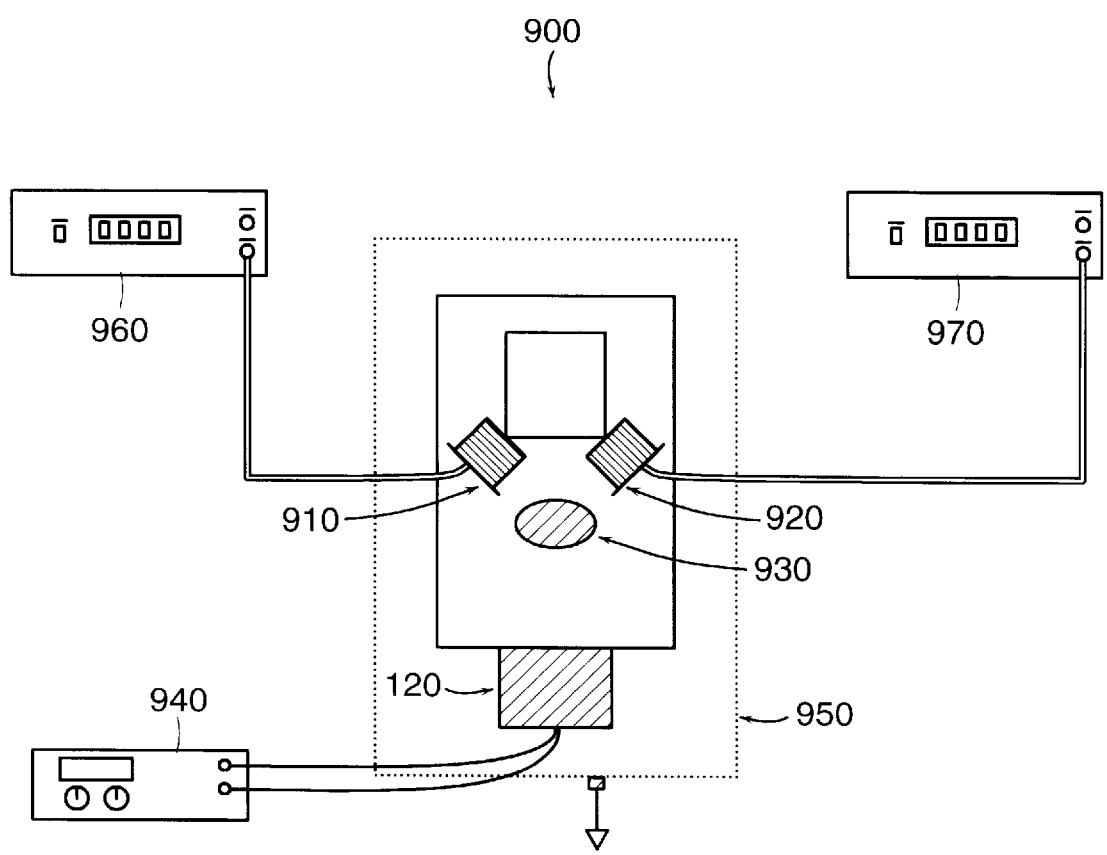
FIG. 9 depicts a testbed apparatus.

FIG. 9 depicts a test fixture used to analyze the sensitivity and specificity of the response of the filtered PIN photodiodes. A sample fluorescin is placed in a cuvette 900. A DC power supply powers filtered light source 120. Filtered light source 120 illuminates the sample fluorescin with 300 nm light. The sample fluorescin, fluoresces in response to the 300 nm light. Photodiode assemblies 910 and 920 emit electrical signals in response to light of 370 mn and 440 nm, respectively. These electrical signals are sent to channel amplifiers 960 and 970, where the intensities of the electrical signals are read. A fiber optic bundle 930 provides access for an external spectrometer (not shown) to corroborate results. The light source 120, the cuvette 900 and the photodiode assemblies 910 and 920 are all enclosed in a light-tight metal enclosure 950.

Figure 10:
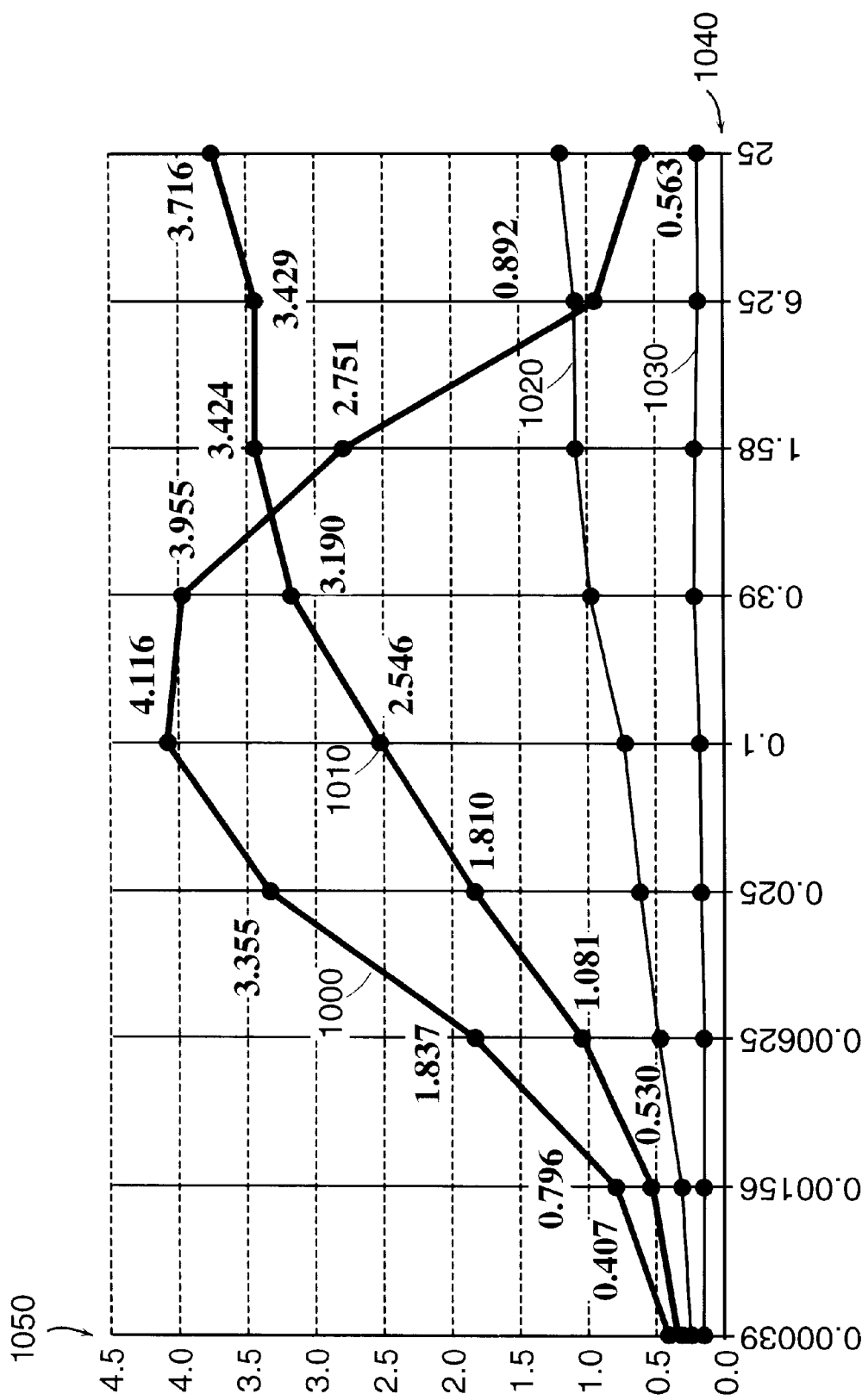
FIG. 10 depicts the on-channel and off-channel sensitivity of the system depicted in FIG. 9.

FIG. 10 depicts the response of each photodiode assembly to each fluorophore. The units along the x-axis 1040 represent fluorophore concentration as a percentage in solution. The units along the y-axis 1050 represent the response of the photodiodes to the light in nanoamperes. Response curve 1000 depicts the response of the test fixture's 440 nm channel amplifier to coumarin, a 460 nm fluorophore. Response curve 1010 depicts the response of the test fixture's 370 nm channel amplifier to PDB, a 370 nm fluorophore. Response curve 1020 depicts the response of the test fixture's 440 nm channel amplifier to PDB, a 370 nm fluorophore. Response curve 1030 depicts the response of the test fixture's 370 nm channel amplifier to coumarin, a 460 nm fluorophore. Intensity of coumarin fluorescence at decreases at higher concentrations due to self-absorption. These results indicate that each sensor responds to its selected wavelength with a high degree of sensitivity and specificity.

Figure 11:
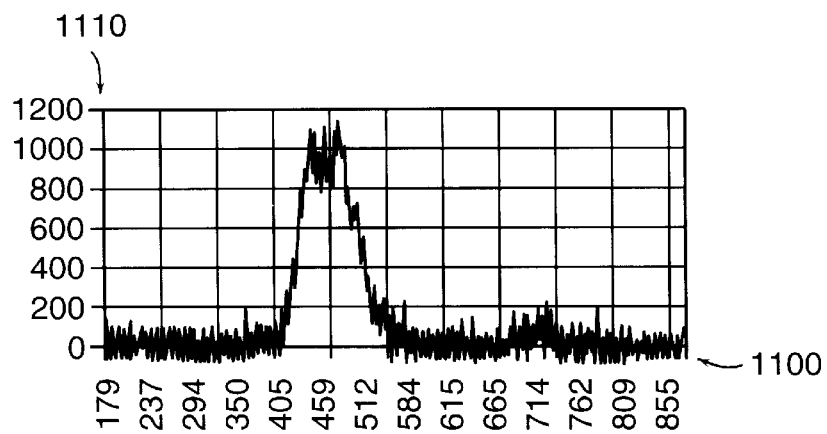
FIG. 11 depicts the spectral response of the coumarin fluorophore to 300 nm light.
Figure 12:
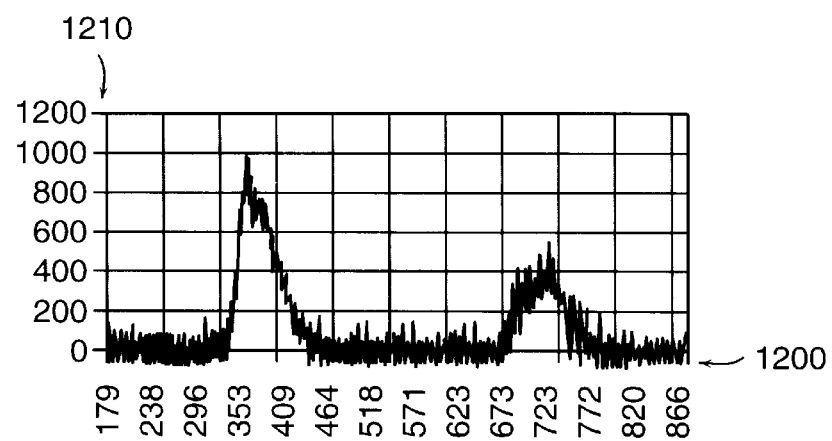
FIG. 12 depicts the spectral response of the PBD fluorophore to 300 nm light.

FIG. 11 depicts the emission spectrum of a 0.1% mixture of the fluorescin coumarin to 300 nm light. The units along the x-axis 1100 represent the wavelength of the light emitted in nanometers. The units along the y-axis 1110 represent the intensity of fluorescence in counts. These results indicate that the majority of coumarin's fluorescence is emitted at wavelengths around 460 nm. FIG. 12 depicts the emission spectrum of a 0.1% mixture of the fluorescin PBD to 300 nm light. The units along the x-axis 1200 represent the wavelength of the light emitted in nanometers. The units along the y-axis 1210 represent the intensity of fluorescence in counts. These results indicate that the majority of PBD's fluorescence is emitted at wavelengths around 370 nm.

Figure 13:
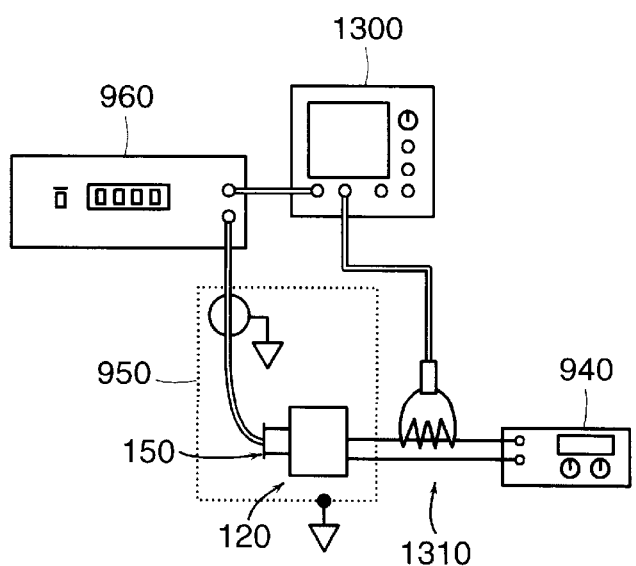
FIG. 13 depicts an excitation source response test setup.
Figure 14:
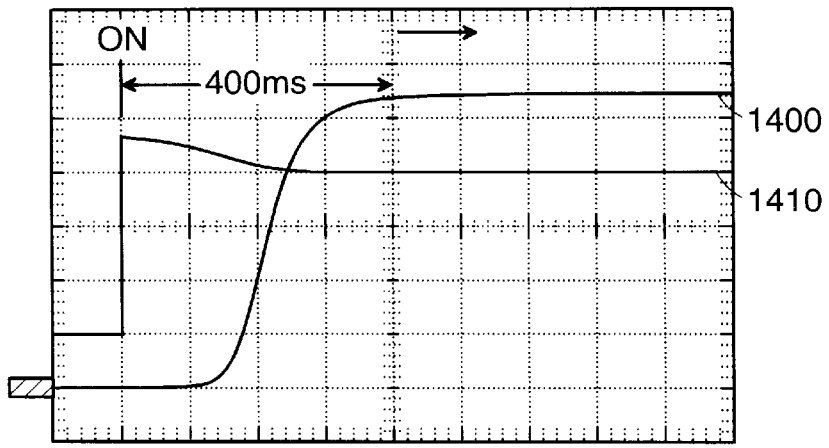
FIG. 14 depicts an excitation source inrush and steady-state characteristics.

FIG. 13 depicts the testing apparatus used to analyze inrush and steady state response of the light source 120 to the application of power. The light source 120 is powered by a DC power supply 940 set at 2.0 amps and 37 volts. One channel of an oscilloscope 1300 is placed across a 25 ohm resistor 1310 placed between power supply 940 and light source 120. Photodiode 150 emits an electrical signal in response to the light output by light source 120. The electrical signal is then sent to an amplifier 960 and then to another channel of oscilloscope 1300. Light source 120 and photodiode 150 are enclosed in a light tight container 950. The signals on the two channels of the oscilloscope 1300 are analyzed to compare light output to power input. FIG. 14 depicts the results of these tests. Response curve 1400 depicts the intensity of the light emitted by the light source 120. Response curve 1410 depicts the current supplied to the light source 120. From these tests, it was determined that the spectrometer would require a power supply of 10.64 watts, and that it took 400 milliseconds from the application of power for the light source to reach full intensity.

Figure 15:
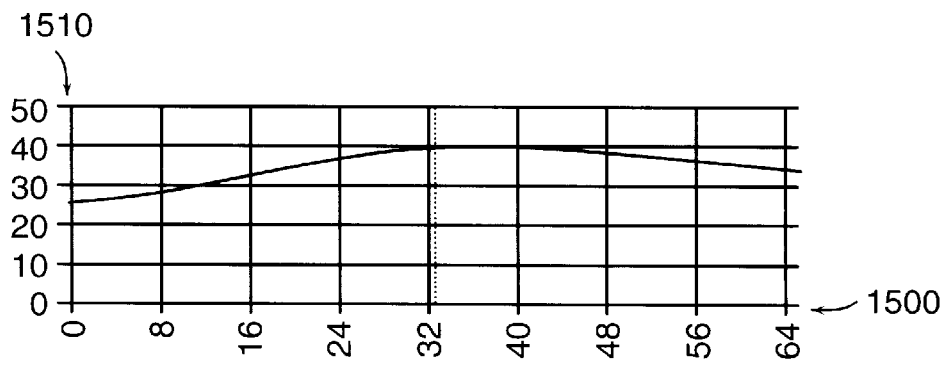
FIG. 15 depicts the exterior temperature of a probe during and after source excitation.

For in vivo use, surface temperature needs to be moderate. FIG. 15 depicts probe surface temperature as a function of time of operation. The units along the x-axis 1500 represent time in seconds. The units along the y-axis 1510 represent the surface temperature of the probe in degrees Celsius. To obtain these measurements, a J-type thermocouple (Omega Engineering, Inc., Stamford, Conn.) model 5TC-GG-J-20-36 was attached to the exterior surface of the embodiment depicted in FIG. 3. The tungsten-halogen bulb 130 of this embodiment has been demonstrated to generate a surface temperature of no more than 40 degrees Celsius after 30 seconds of continuous operation. To prevent an undue increase in surface temperature, the light source 120 can be operated intermittently or with short excitation times.

Figure 16A:
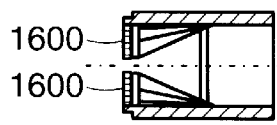
FIG. 16 depicts two possible geometric configurations for a pair of sensors.
Figure 16C:
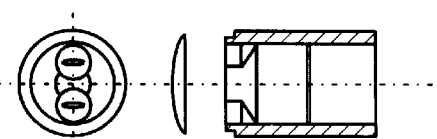
Figure 16B:
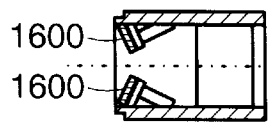
Figure 17:
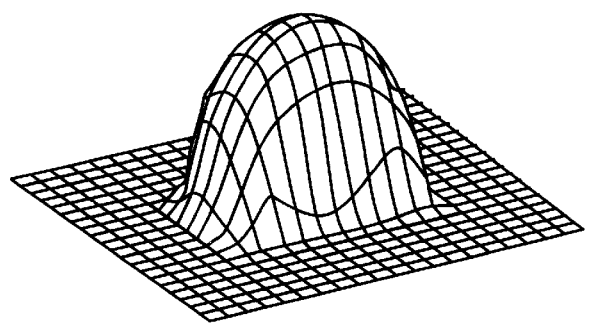
FIG. 17 depicts an excitation source radiation pattern
Figure 18:
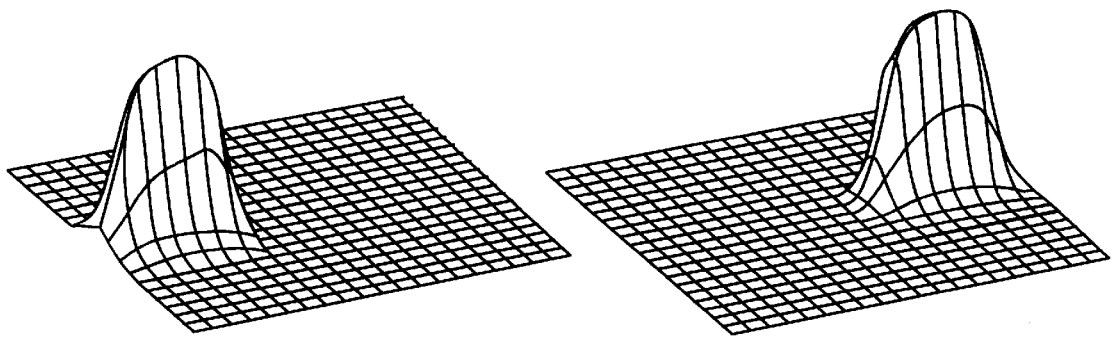
FIG. 18 depicts the spatial response of a sensor pair in a coplanar configuration.
Figure 19:
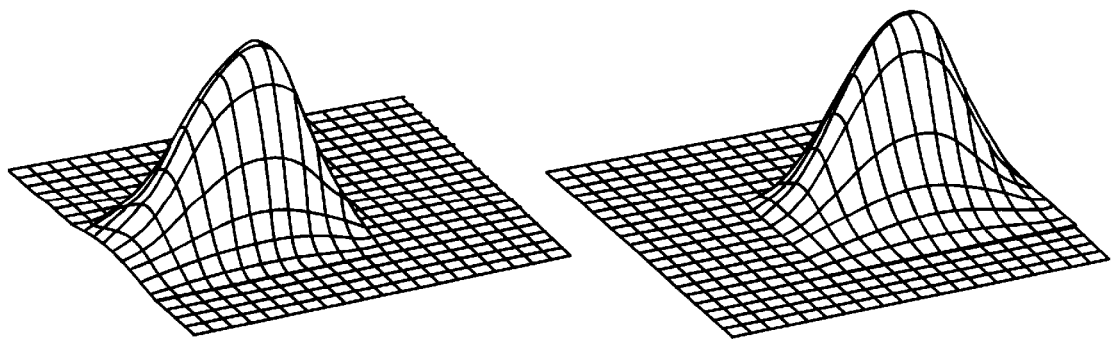
FIG. 19 depicts the spatial response of a sensor pair in an angled configuration.

The spatial characteristics of the sensors effect the sensitivity of the spectrometer. FIG. 16 depicts two possible spatial configurations for an array pair 1600 of sensors. FIG. 16(a) depicts the array pair 1600 as coplanar, while FIG. 16(b) depicts the array pair 1600 angled inwards toward the light source (not shown). FIG. 17 depicts the radiation pattern of the excitation source. FIG. 18 depicts the response pattern for an array pair in a coplanar configuration. FIG. 19 depicts the response pattern for an array pair in an inwardly angled configuration. These results indicate that angling the array pair may improve system sensitivity.

Figure 20:
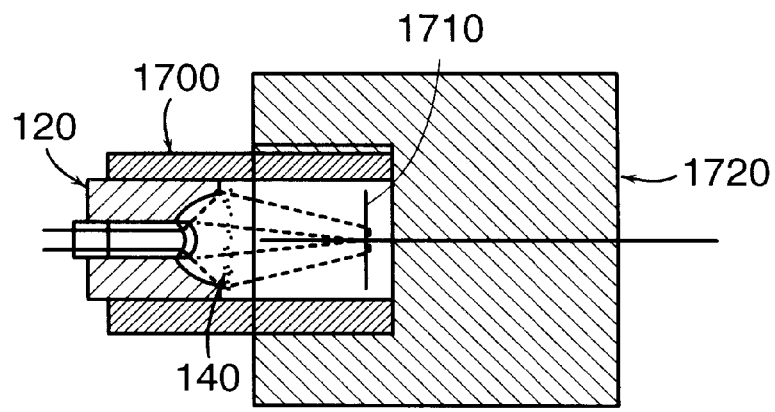
FIG. 20 depicts apparatus for measuring the power output of an excitation source.

The spectrometer must be able to operate within certain parameters so as not to cause tissue damage. For example, it is desirable to keep the surface temperature of the spectrometer to a minimum. In order to minimize waste heat generated by the spectrometer, it is therefore desirable to obtain fluorescence readings with the minimal amount of excitation energy. FIG. 20 depicts apparatus used to measure the power output of an excitation energy source, such as a light source. In this apparatus, the light source 120 and its filter 140 is attached to a Newport radiometer head 1720 by means of an adapter 1700. The detector 1710 measures the power output of the light source 120. In a preferred embodiment of the spectrometer, the sensors are able to obtain fluorescence readings using an excitation energy as low as 200 $\mu$W.

Figure 21:
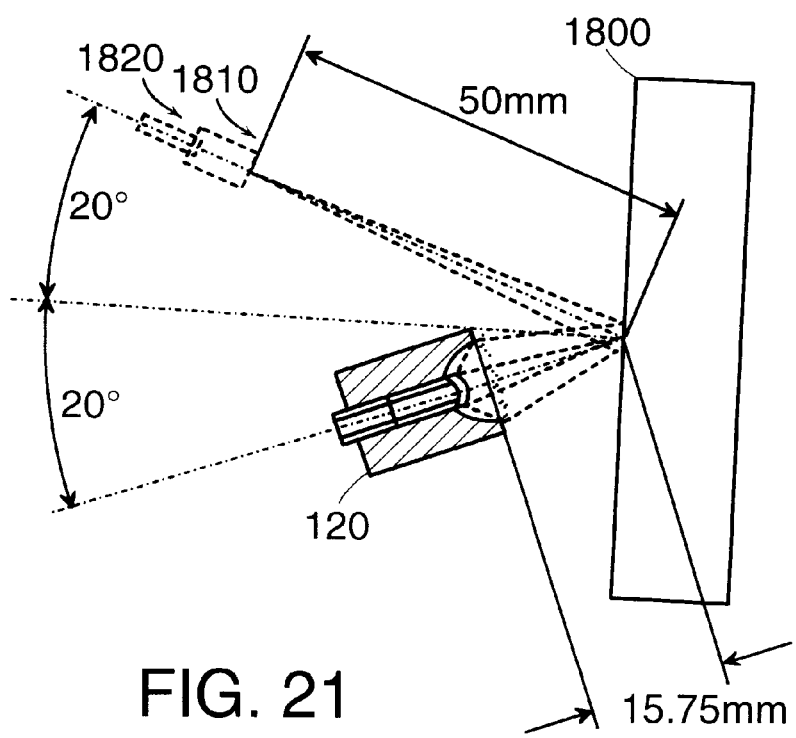
FIG. 21 depicts apparatus for measuring sensor efficiency.

FIG. 21 depicts a test fixture used to measure the response and efficiency of the PIN photodiodes. A baseline value was first obtained by shining light source 120 onto reflectance standard 1800 and measuring reflected light using an advanced PhotonX detector 1820. The reflectance standard was then replaced with an uncalibrated fluorescence standard and the unfiltered photodiode 1820 was replaced with a photodiode with a bandpass filter centered at 442 nm. A fluorescence signal of 4.1 nW was recorded, which is about 10% of the reflected signal from a white target.

While certain embodiments have been used to illustrate the invention, it will be recognized by those skilled in the art that various modifications can be made therein without departing from the scope of the invention as claimed.

What is claimed is:

1. An interventional device having a length and a distal end and a proximal end, comprising:
    a spectrometer disposed at the distal end, said spectrometer comprising
        a source unit for emitting light at a wavelength sufficient to induce fluorescence of tissue,
        a plurality of sensors, each of the sensors capable of detecting light at a wavelength at which the tissue fluoresces and emitting an electrical signal in response to detected light, and
        electronics for processing the electrical signal emitted by each of the sensors; and
    at least one electrical conduit extending from the spectrometer, within and along the length of the device, and to the proximal end of the device.

2. The interventional device of claim 1 wherein said source unit comprises a light source and a filter.

3. The interventional device of claim 2 wherein the light source comprises a tungsten-halogen lamp.

4. The interventional device of claim 2 wherein the filter comprises a bichromatic filter.

5. The interventional device of claim 4 wherein the bichromatic filter allows light of about 300 nm wavelength to pass.

6. The interventional device of claim 4 wherein the bichromatic filter allows light of about 710 mn wavelength to pass.

7. The interventional device of claim 4 wherein the bichromatic filter allows light of about 300 nm wavelength and about 710 nm wavelength to pass.

8. The interventional device of claim 1 wherein the source unit emits light at wavelengths between 420 nm and 490 nm.

9. The interventional device of claim 1 wherein one of the plurality of sensors comprises a bandpass filter that allows light of about 370 nm wavelength to pass.

10. The interventional device of claim 1 wherein one of the plurality of sensors comprises a bandpass filter that allows light of about 440 nm wavelengths to pass.

11. The interventional device of claim 1 wherein one of the plurality of sensors comprises a bandpass filter that allows light of about 370 nm wavelength to pass and another one of the plurality of sensors comprises a bandpass filter that allows light of about 440 nm wavelength to pass.

12. The interventional device of claim 1 wherein said source unit outputs an excitation power of 200 $\mu$w.

13. The interventional device of claim 1 wherein the electronics comprise an amplifier and a comparator.

14. The interventional device of claim 1 wherein a surface temperature of said distal end remains below about 40° C. in less than 30 seconds of continuous operation.

15. The interventional device of claim 1 wherein the source unit comprises a monochromatic light source.

16. The interventional device of claim 15 wherein said monochromatic light source comprises a light-emitting diode.

17. The interventional device of claim 15 wherein said monochromatic light source emits light at a frequency of about 435 nm.

18. The interventional device of claim 15 wherein said monochromatic light source comprises a light emitting diode emitting light at a frequency of about 435 nm.

* * * * *